(12) United States Patent
Giangrande et al.

(10) Patent No.: US 9,029,805 B2
(45) Date of Patent: May 12, 2015

(54) METHOD FOR INSPECTING CONTACT BETWEEN MATING GEARS

(71) Applicant: American Axle & Manufacturing, Inc., Detroit, MI (US)

(72) Inventors: Holly A. Giangrande, Troy, MI (US); Ryan M. Trevino, Waterford, MI (US); Thomas M. Sep, Linden, MI (US); Lee Holloway, Southfield, MI (US)

(73) Assignee: American Axle & Manufacturing, Inc., Detroit, MI (US)

( * ) Notice: Subject to any disclaimer, the term of this patent is extended or adjusted under 35 U.S.C. 154(b) by 210 days.

(21) Appl. No.: 13/775,572

(22) Filed: Feb. 25, 2013

(65) Prior Publication Data

US 2014/0239194 A1 Aug. 28, 2014

(51) Int. Cl.
*G01N 21/91* (2006.01)

(52) U.S. Cl.
CPC ..................... *G01N 21/91* (2013.01)

(58) Field of Classification Search
CPC .. G01M 13/021; G01B 11/2416; G01N 21/91
USPC ................................................. 250/459.1
See application file for complete search history.

(56) References Cited

U.S. PATENT DOCUMENTS

| | | | |
|---|---|---|---|
| 4,618,256 A | 10/1986 | Bartolomeo | |
| 5,083,458 A | 1/1992 | DeGeorge et al. | |
| 5,373,735 A | 12/1994 | Gutman | |
| 6,148,098 A | 11/2000 | Rutschke et al. | |
| 6,174,223 B1 | 1/2001 | Miyamae et al. | |
| 6,864,489 B2 | 3/2005 | Chen et al. | |
| 8,167,758 B2 | 5/2012 | Downs et al. | |
| 8,180,143 B2 | 5/2012 | George et al. | |
| 2003/0000418 A1* | 1/2003 | Boulos ........................ 106/14.21 |
| 2004/0192564 A1 | 9/2004 | Balasubramaniam et al. | |
| 2007/0058854 A1 | 3/2007 | Caskey et al. | |

FOREIGN PATENT DOCUMENTS

| | | |
|---|---|---|
| JP | 2985191 B2 | 11/1999 |
| JP | 2010266244 A | 11/2010 |

OTHER PUBLICATIONS

"Adding Dye to Chevron Industrial Oil Products", Technical Bulletin, Jan. 2011, available at http://spencerbrothersinc.com/assets/LTB-38-Dye-Tech-Bulletin.pdf.*

(Continued)

*Primary Examiner* — David J Makiya
*Assistant Examiner* — Kenneth J Malkowski
(74) *Attorney, Agent, or Firm* — Harness, Dickey & Pierce, P.L.C.

(57) ABSTRACT

A method for inspecting contact between mating gears that includes applying a mixture to teeth of a first gear, teeth of a second gear, or the teeth of both the first and second gears. The mixture includes a lubricating oil and a fluorescing dye. The first gear is rotated to drive the second gear. While the second gear is being driven by the first gear, electromagnetic radiation, such as ultra-violet radiation, is applied to the teeth of at least one of the first and second gears to cause the teeth to fluoresce. The fluorescing teeth of the second gear are inspected to identify a tooth inspection zone that approximates a zone of contact between the teeth of the first and second gears.

16 Claims, 5 Drawing Sheets

(56) References Cited

OTHER PUBLICATIONS

Section 5/4/2C—Reading and Adjusting the Ring & Pinion Tooth Pattern, *Differentials Identification, Restoration & Repair, 2nd Edition*, J. Allen & R. Lyman (2010).

Ring and Pinion Tooth Contact Pattern Information, Dana® Spicer® Drive Axles P/N: SHAIS168 (2005).

Hi-Performance Ring & Pinions Installation Instructions, Richmond Gear (Sep. 2003).

* cited by examiner

METHOD FOR INSPECTING CONTACT BETWEEN MATING GEARS

FIELD

The present disclosure generally relates to a method for inspecting contact between mating gears.

BACKGROUND

This section provides background information related to the present disclosure which is not necessarily prior art.

Automotive axle assemblies typically include a hypoid input pinion that is meshingly engaged to a bevel ring gear. During manufacturing of the hypoid input pinion and the ring gear and/or the assembly process for an axle assembly, it is common practice to visually inspect the contact area between the mating teeth of the hypoid input pinion and the bevel ring gear. While some have suggested the use of sophisticated inspection tooling, it is common practice to use a conventional gear marking compound. For example, a gear marking compound can be applied to the bevel ring gear; the hypoid input pinion can be rotated several revolutions to mesh the teeth of the hypoid input pinion with the teeth of the bevel ring gear; and because the teeth of the hypoid input pinion slide to a degree on the teeth of the bevel ring gear as they are meshed with one another, the gear marking compound is scraped or worn off in the area where the teeth of the hypoid input pinion contact the teeth of the bevel ring gear.

In some respects, the use of conventional gear marking compounds is disadvantageous because the gear marking compound is messy and can be difficult to remove after the inspection process. Accordingly, an improved method for inspecting contact between mating gears is needed.

SUMMARY

This section provides a general summary of the disclosure, and is not a comprehensive disclosure of its full scope or all of its features.

In one form, the present teachings provide a method for inspecting contact between mating gears. The method includes: providing first and second gears, each of the first and second gears having respective sets of gear teeth; mounting the first and second gears for rotation about respective axes such that the teeth of the first gear being meshed to the teeth of the second gear; applying a mixture to the teeth of the first gear, the teeth of the second gear, or the teeth of both the first and second gears, the mixture comprising a lubricating oil and a fluorescing dye; rotating the first gear relative to the housing to thereby drive the second gear; applying ultra-violet radiation to the teeth of at least one of the first and second gears while the first gear is being rotated to thereby drive the second gear; and inspecting the ultra-violet radiated teeth to identify a tooth inspection zone that approximates a zone of contact between the teeth of the first and second gears.

In another form, the present teachings provide a method for inspecting contact between mating gears. The method includes: providing an assembly having a housing, an input pinion gear and a ring gear, the housing supporting the input pinion gear and the ring gear for rotation about respective axes, the input pinion gear and the ring gear having respective sets of teeth, the teeth of the input pinion gear being meshed to the teeth of the ring gear; applying a mixture to the teeth of the input pinion gear, the teeth of the ring gear, or the teeth of both the input pinion gear and the ring gear; rotating the input pinion gear relative to the housing to thereby drive the ring gear; exposing the portion of the mixture on the teeth of the ring gear to electromagnetic radiation to cause the mixture to fluoresce; and inspecting the fluorescing mixture on the teeth of the ring gear to identify a tooth inspection zone that is indicative of a zone of contact between the teeth of the input pinion gear and the ring gear.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
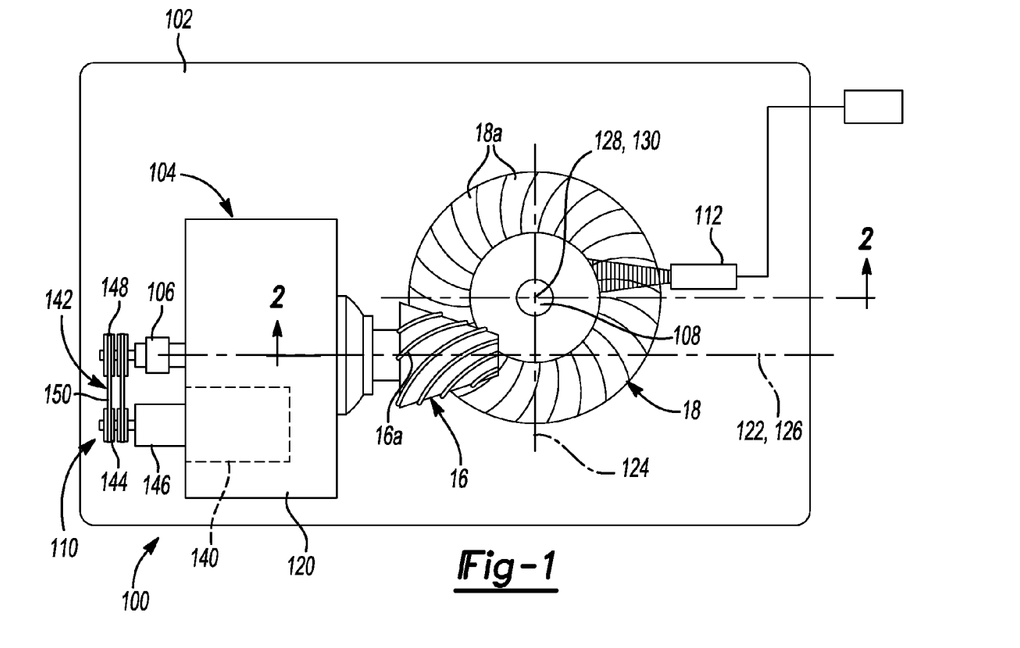
FIG. 1 is a top plan view of an exemplary gear inspection machine for performing a gear inspection method in accordance with the teachings of the present disclosure.
Figure 2:
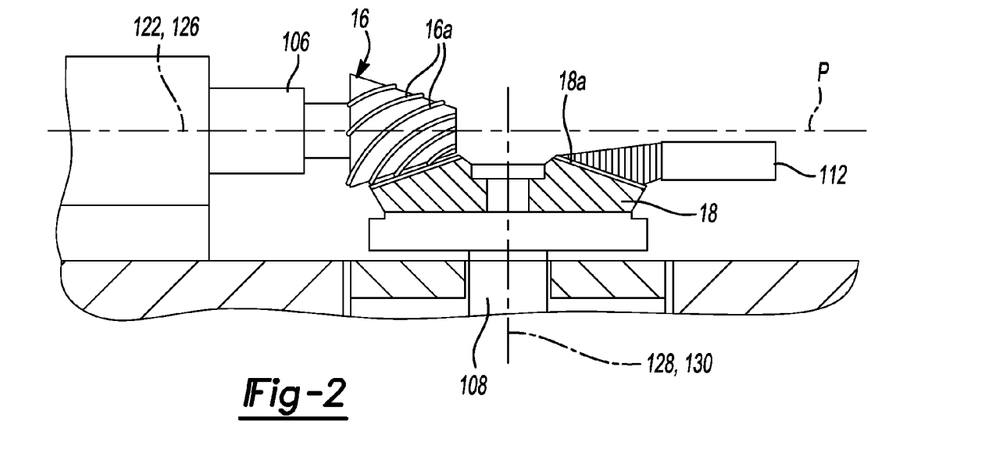
FIG. 2 is a section view taken along the line 2-2 of FIG. 1.

With reference to FIGS. 1 and 2, an exemplary gear inspection machine for performing a method for inspecting contact between mating gears in accordance with the teachings of the present disclosure is generally indicated by reference numeral 100. The gear inspection machine 100 can be configured to help collect, collect and/or analyze data associated with the quality of meshing between teeth 16a of a first gear 16 and teeth 18a of a second gear 18. In the particular example provided, the first gear 16 is a hypoid spiral bevel pinion gear and the second gear 18 is a hypoid spiral bevel ring gear. It will be appreciated, however, that the teachings of the present disclosure have application to other gear types and as such, spiral gears and spur gears.

The gear inspection machine 100 can include a base 102, a carriage mechanism 104, a first spindle 106, a second spindle 108, a rotary power source 110 and an electromagnetic radiation source 112. The carriage mechanism 104 can comprises a carriage 120 that can be mounted to the base 102 for movement along first (X) and second (Y) axes 122 and 124, respectively. The first (X) and second (Y) axes 122 and 124 are perpendicular to one another and are disposed in a reference plane P. The first spindle 106 can be rotatably mounted to the carriage 120 so that a rotational axis 126 of the first spindle 106 is coincident with the first (X) axis 122 and disposed in the reference plane P. The second spindle 108 is mounted to the base 102 for rotation about a rotational axis 128 that is perpendicular to the reference plane P and the rotational axis 126 of the first spindle 106. The second spindle 108 can be extended or retracted along a third (Z) axis 130 that can be coincident with the rotational axis 128. The rotary power source 110 can comprise any means for providing rotary power to the first spindle 106. For example, the first spindle 106 can be directly driven by an electric motor. In the particular example provided, the rotary power source 110 comprises an electric motor 140 that drives the first spindle 106 through a belt drive system 142 having a first pulley 144, which is mounted to the output shaft 146 of the electric motor 140 for rotation therewith, a second pulley 148, which is non-rotatably coupled to the first spindle 106, and a belt 150 that is configured to transmit rotary power between the first and second pulleys 144 and 148. The electromagnetic radiation source 112 can be mounted to the base 102 or can be hand-held by an operator/technician and can produce electromagnetic radiation that can be directed at the teeth 16a of the first gear 16 and/or the teeth 18a of the second gear 18.

Figure 3:
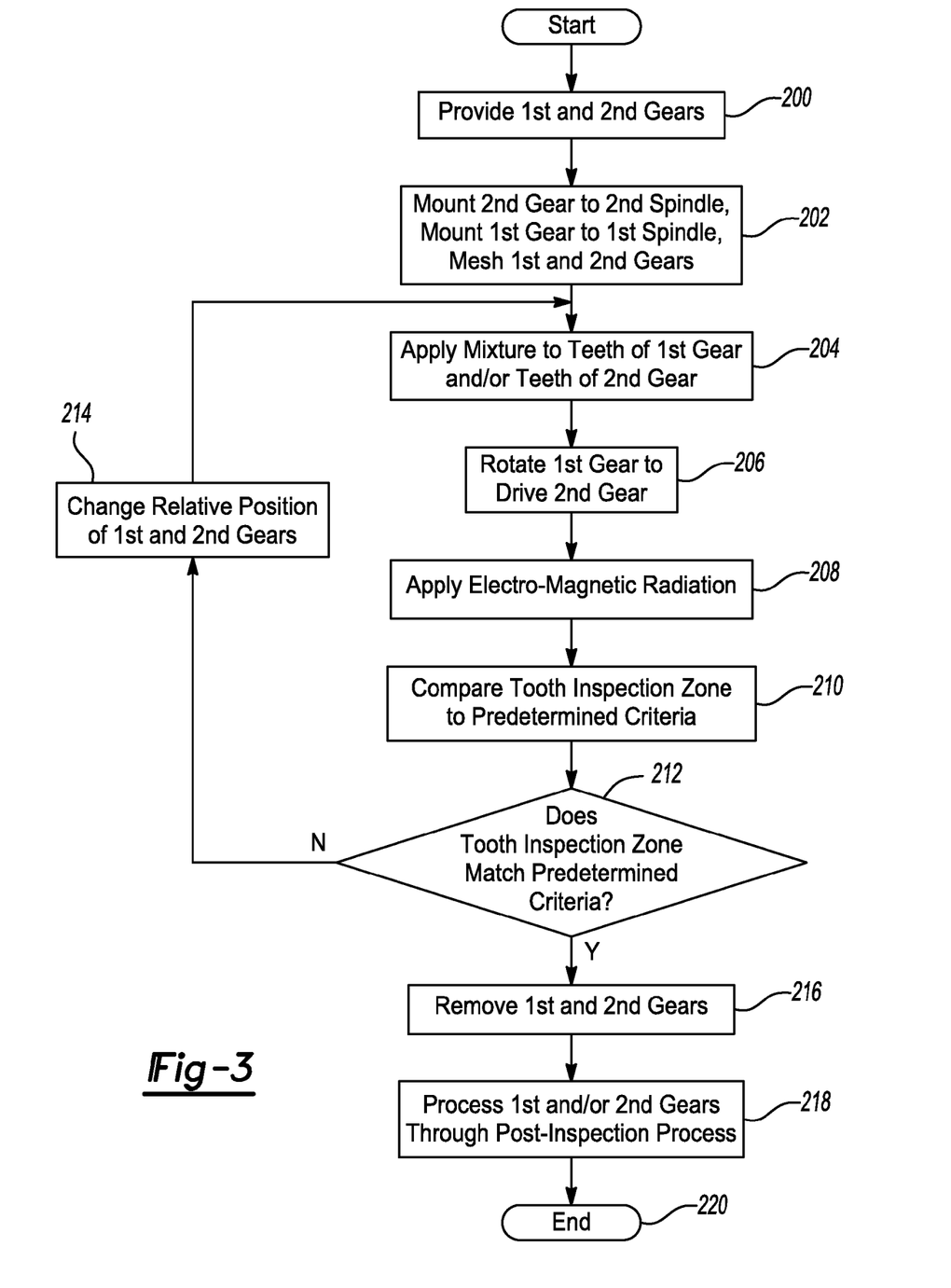
FIG. 3 is a schematic illustration in flow-chart form of an exemplary method in accordance with the teachings of the present disclosure.

With additional reference to FIG. 3, a method for inspecting contact between mating gears in accordance with the teachings of the present disclosure is schematically illustrated. The method can begin at block 200 where the first and second gears 16 and 18 are provided. The method can proceed to block 202 where the second gear 18 is mounted to the second spindle 108, the first gear 16 is mounted to the first spindle 106, and the teeth 16a of the first gear 16 are meshingly engaged to the teeth 18a of the second gear 18.

The method can proceed to block 204 where a mixture can be applied to the teeth 16a of the first gear 16 and/or to the teeth 18a of the second gear 18. The mixture can comprise a suitable lubricating oil and a fluorescing dye. Any desired lubricating oil can be used, but in the particular example provided, we employed an 80W-90 hypoid gear lubricant conforming to the API-GL5 standard. Any desired fluorescent dye can be used, but in the particular example provided, we used a fluorescent dye marketed by General Motors Corporation as their "4-in-1 Fluorescent Dye", part number 88861206. The ratio of fluorescent dye to lubricating oil can be relatively small. For example, we employed a ratio of 0.2 ml of fluorescent dye to 4,000 ml of lubricating oil to obtain a desired level of brightness when the dye fluoresces. It will be appreciated, however, that smaller or larger ratios than that described herein can nonetheless be effective and as such, the scope of the present disclosure is not limited to any particular ratio fluorescent dye to lubricating oil. The method can proceed to block 206.

Figure 4:
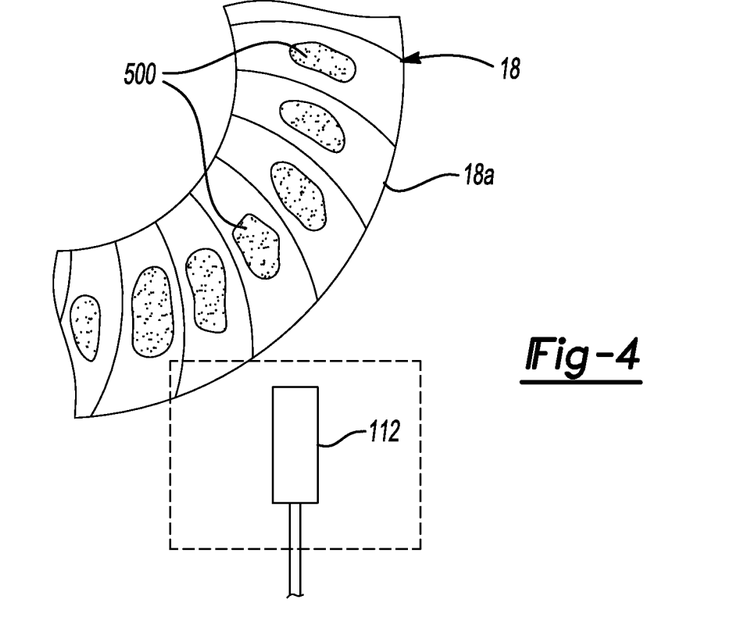
FIG. 4 is an enlarged portion of FIG. 1 illustrating a tooth inspection zone.

In block 206 the first gear 16 is rotated (i.e., via the rotary power source 110 in the particular example provided) to thereby drive the second gear 18. The methodology can proceed to block 208 where the electromagnetic radiation source 112 is operated while the second gear 18 is being driven by the first gear 16 to cause the fluorescent dye on the teeth 16a of the first gear 16 and/or the teeth 18a on the second gear 18 to fluoresce. With reference to FIG. 4, any suitable electromagnetic radiation source 112 that is compatible with the fluorescent dye can be employed, but in the particular example provided, the electromagnetic radiation source 112 comprised an ultra-violet (UV) light source that was directed onto the teeth 18a of the second gear 18. Energy from the electromagnetic radiation source 112 can be absorbed by the fluorescent dye, causing the fluorescent dye in the mixture on the teeth 18 of the second gear 18 to fluoresce and thereby illuminate the teeth 18a of the second gear 18. Contact between the teeth 16a of the first gear 16 and the teeth 18a of the second gear 18 can wipe or scrape the mixture off of the teeth 18a on the second gear 18 where the teeth 16a and 18a contact one another. Accordingly, a portion of each tooth 18a of the second gear 18, hereinafter referred to as a "tooth inspection zone 500", will be covered with less of the mixture (or none of the mixture) and as such, will appear as a dark spot since a corresponding lesser amount of dye will be present in the tooth inspection zone 500. For various reasons, the tooth inspection zone 500 will only approximate the area over which the teeth 16a and 18a contact one another. In this regard, the tooth inspection zone 500 is not necessarily the area over which the teeth 16a and 18a contact one another because the mixture is a viscous fluid and its position on any one of the teeth 16a and 18a can vary over time due to the effects of gravity and/or centrifugal force.

With reference to FIGS. 2-4, the method can proceed to block 210 where the tooth inspection zone 500 can be compared to a predetermined set of inspection criteria to determine if the first and second gears 16 and 18 are meshing in a desired manner. For example, the tooth inspection zone 500 can be evaluated to determine if it is positioned in a desired location and/or sized in a desired manner. The method can proceed to decision block 212.

In decision block 212, if the tooth inspection zone 500 is not in the desired location or sized in the desired manner, the methodology can proceed to block 214 where relative positioning between the first and second gears 16 and 18 can be adjusted. In the example provided, the first gear 16 may be moved along the X axis 122 (FIG. 1) and/or the Y axis 124 (FIG. 1), while the second gear 18 may be moved along the Z axis 130. The method can loop back to block 204.

Returning to decision block 212, if the tooth inspection zone 500 is positioned in the desired location and sized in a desired manner, the method can proceed to block 216 where the first and second gears 16 and 18 are removed from the first and second spindles 106 and 108, respectively. Optionally, the method can proceed to block 218 where the first gear 16 and/or the second gear 18 can be processed through one or more post-inspection operations. For example, one or both of the first and second gears 16 and 18 can be cleaned and processed through a conversion coating operation where a conversion coating can be formed on the teeth 16a of the first gear 16 and/or the teeth 16b of the second gear 18. In the particular example provided, both the first and second gears 16 and 18 are processed through a conversion coating operation in which manganese phosphate crystals are formed on the surface of the teeth 16a and 16b. The methodology can proceed to block 220 where the methodology can terminate.

Figure 5:
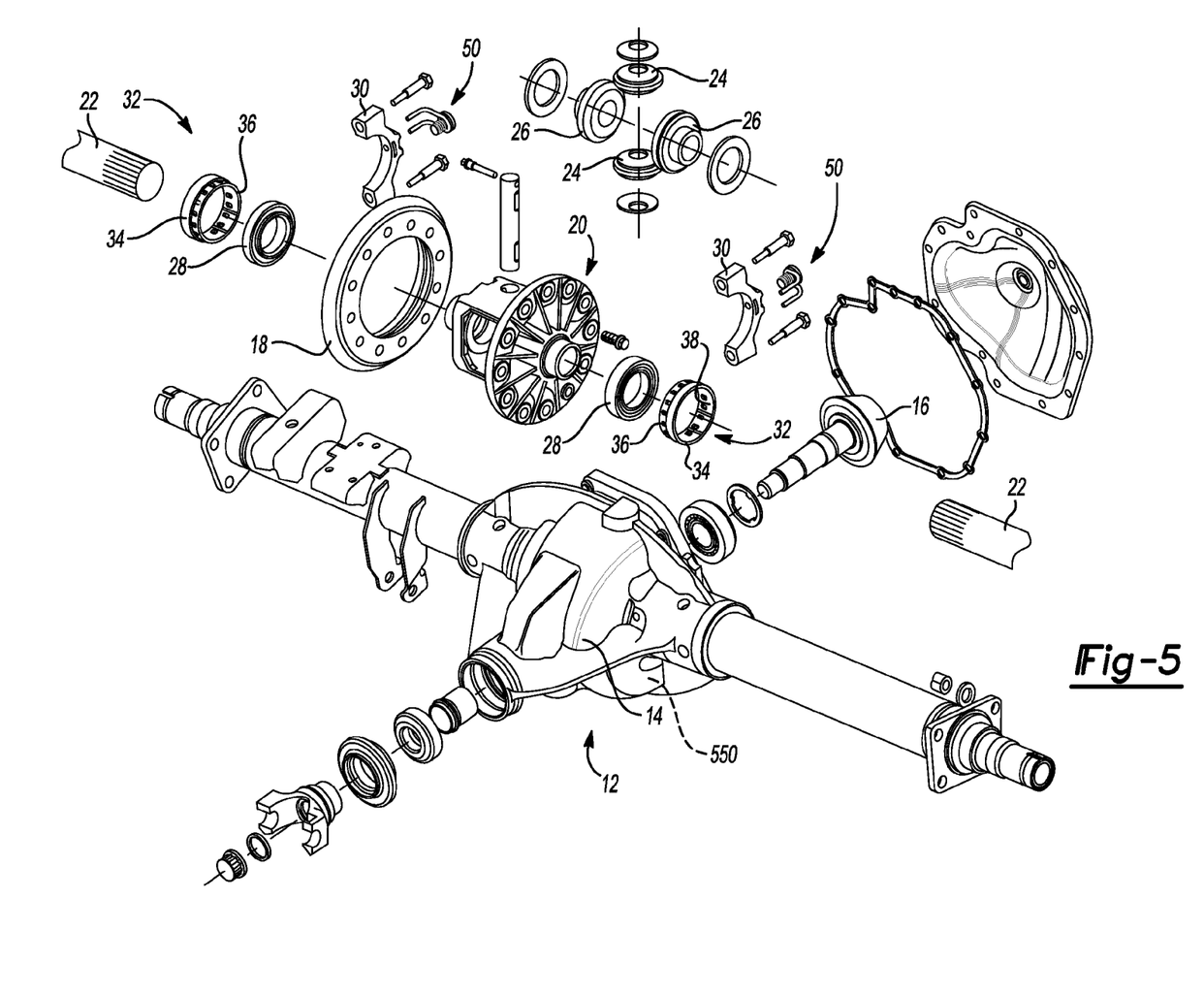
FIG. 5 is an exploded perspective view of an exemplary axle assembly having a pair of meshing gears that have been inspected in accordance with the teachings of the present disclosure.

While the above-methodology has been described in association with a gear inspection machine 100, it will be appreciated that the teachings of the present disclosure have broader application. For example, the teachings of the present disclosure can be employed to inspect a tooth inspection zone on the teeth of a ring gear in an axle assembly. With reference to FIG. 5, an exemplary axle assembly is generally indicated by reference numeral 12. The axle assembly 12 can include an axle housing 14 in which a hypoid pinion gear 16 and a ring gear 18 are rotatably mounted. The ring gear 18 is drivingly interconnected to a differential assembly 20 that functions to transfer power to a pair of axle shafts 22 (only partly shown) while compensating for any difference in axle shaft speed rotation as may occur during a turn or other steering maneuver. The differential assembly 20 can include a pair of pinion gears 24 and a pair of side gears 26 that are meshed with the pinion gears 24 and drivingly interconnected to the axle shafts 22. The differential assembly 20 can be supported for rotation relative to the axle housing 14 via a pair of differential bearings 28. More specifically, the axle housing 14 can include two semi-circular bulkheads (not shown) for supporting approximately 180 degrees of the circumference of each of the differential bearings 28. A pair of bearing caps 30 can journally support the remaining approximate one-half of each of the differential bearings 28. Each bearing cap 30 can be mounted to a corresponding one of the bulkheads via a pair of threaded fasteners.

Figure 6:
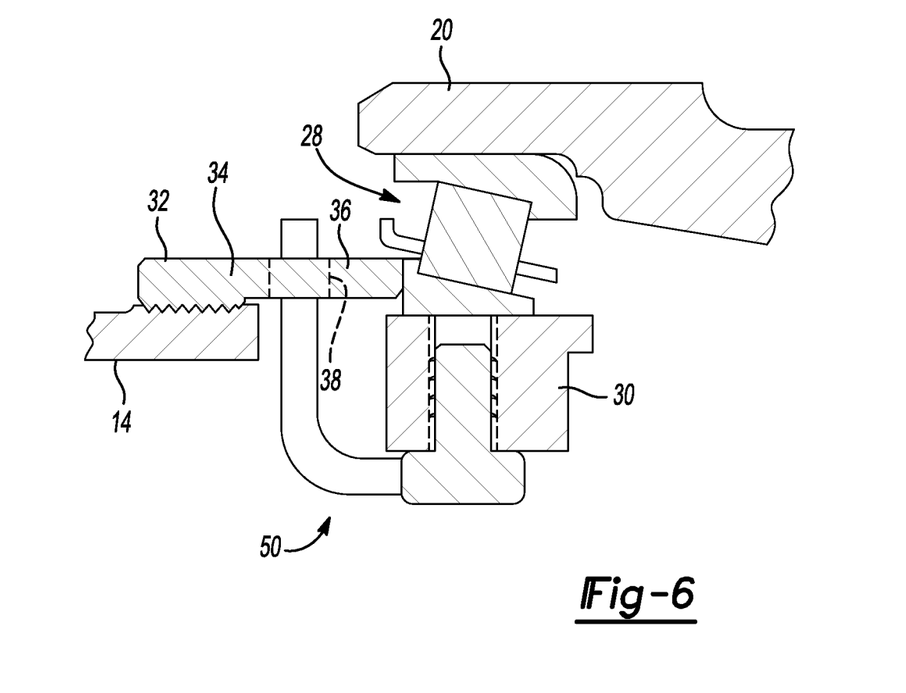
FIG. 6 is a sectional view of a portion of the axle assembly of FIG. 1.

A pair of adjustment nuts 32 are provided to permit meshing engagement between the pinion gear 16 and the ring gear 18 to be adjusted. With additional reference to FIG. 6, each adjustment nut 32 can have a first end 34, which can be threadingly engaged to the axle housing 14 (i.e., the bulkhead and the bearing cap 30) and a second end 36 that can abut the differential bearing 28. It will be appreciated that coordinated rotation of the adjustment nuts 32 in a predetermined rotational direction can axially displace the differential bearings 28 to thereby axially displace the ring gear 18 relative to the pinion gear 16. Each adjustment nut 32 can further include a plurality of retention apertures or slots 38 for receipt of a portion of an adjuster lock 50. The adjuster lock 50 can interconnect the adjustment nut 32 and the bearing cap 30 to prevent relative rotation there between.

Figure 7:
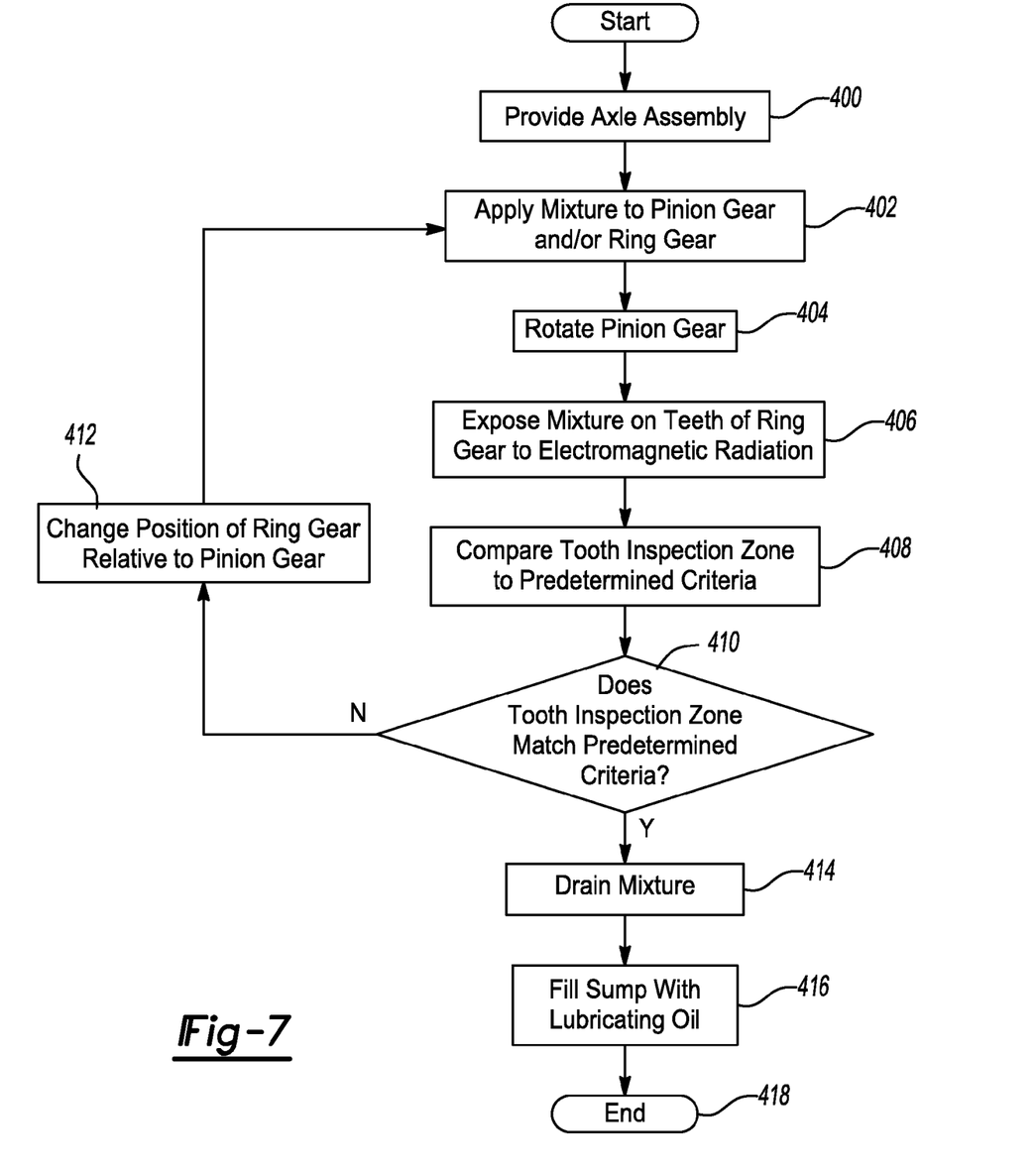
FIG. 7 is a schematic illustration in flow-chart form of a second exemplary method in accordance with the teachings of the present disclosure.

With additional reference to FIG. 7, a second method for inspecting contact between mating gears in accordance with the teachings of the present disclosure is schematically illustrated. The method can begin at block 400 where the axle assembly 12 is provided. The method can proceed to block 402, where the mixture (described above as comprising a lubricating oil and a fluorescent dye) is applied to the teeth 16a of the pinion gear 16 and/or the teeth 18a of the ring gear 18. The method proceeds to block 404 where the pinion gear 16 is rotated relative to the axle housing 14 to thereby drive the ring gear 18. The method can proceed to block 406 where the portion of the mixture on the teeth 18a of the ring gear 18 can be exposed to electromagnetic radiation (e.g., ultra-violet light) to cause the mixture to fluoresce while the ring gear 18 is being driven by the pinion gear 16. As will be appreciated from the discussion above, contact between the teeth 16a of the pinion gear 16 and the teeth 18a of the ring gear 18 can wipe or scrape the mixture off of the teeth 18a on the ring gear where the teeth 16a and 18a contact one another. Accordingly, a portion of each tooth 18a of the ring gear 18, hereinafter referred to as the "tooth inspection zone 500", will be covered with less of the mixture (or none of the mixture) and as such, will appear as a dark spot since a corresponding lesser amount of dye will be present in the tooth inspection zone 500. The method can proceed to block 408.

In block 408, the tooth inspection zone 500 can be compared to a predetermined set of inspection criteria to determine if the pinion gear 16 and the ring gear 18 are meshing in a desired manner. For example, the tooth inspection zone 500 can be evaluated to determine if it is positioned in a desired location and/or sized in a desired manner. The method can proceed to decision block 410.

In decision block 410, if the tooth inspection zone 500 is not in the desired location or sized in the desired manner, the methodology can proceed to block 412 where relative positioning between the pinion gear 16 and the ring gear 18 can be adjusted. In the example provided, the adjustment nuts 32 can be rotated in a coordinated manner and a desired rotational direction can axially displace the differential bearings 28 to thereby axially displace the ring gear 18 relative to the pinion gear 16 along the Z-axis 130 in a desired manner. The method can loop back to block 402. Returning to decision block 410, if the tooth inspection zone 500 is positioned in the desired location and sized in a desired manner the adjuster locks 50 can be installed to the bearing caps 30 and the adjustment nuts 32 and the method can proceed to block 414 where the mixture is optionally drained from the axle housing 14. The methodology can proceed to block 416 where a quantity of the lubricating oil can be introduced to the axle housing 14 to fill a sump 550 in the axle housing 14 with the lubricating oil. The methodology can proceed to block 418 where the method terminates.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for inspecting contact between mating gears, the method comprising:
    providing first and second gears, each of the first and second gears having respective sets of gear teeth;
    mounting the first and second gears for rotation about respective axes such that the teeth of the first gear being meshed to the teeth of the second gear;
    applying a mixture to the teeth of the first gear, the teeth of the second gear, or the teeth of both the first and second gears, the mixture comprising a hypoid gear lubricant and a fluorescing dye;
    rotating the first gear relative to the housing to thereby drive the second gear;
    applying ultra-violet radiation to the teeth of at least one of the first and second gears while the second gear is being driven by the first gear; and
    inspecting the ultra-violet radiated teeth to identify a tooth inspection zone that approximates a zone of contact between the teeth of the first and second gears.

2. The method of claim 1, further comprising determining if the tooth inspection zone is positioned in a desired location.

3. The method of claim 2, further comprising determining if the tooth inspection zone is sized in a desired manner.

4. The method of claim 2, further comprising adjusting the relative position of the first and second gears if the tooth inspection zone is not positioned in the desired location.

5. The method of claim 1, wherein an amount that is less than or equal to 0.2 ml of the fluorescing dye is contained in 4000 ml of the hypoid gear lubricant.

6. The method of claim 1, wherein after the tooth inspection zone has been inspected, the method further comprises forming a conversion coating on the teeth of the first gear, the teeth of the second gear, or both the teeth of the first gear and the teeth of the second gear.

7. The method of claim 6, wherein the conversion coating comprises manganese phosphate crystals.

8. The method of claim 1, wherein the first and second gears are bevel gears.

9. The method of claim 8, wherein the first and second gears are hypoid gears.

10. A method for inspecting contact between mating gears, the method comprising: providing an assembly having a housing, an input pinion gear and a ring gear, the housing supporting the input pinion gear and the ring gear for rotation about respective axes, the input pinion gear and the ring gear having respective sets of teeth, the teeth of the input pinion gear being meshed to the teeth of the ring gear; applying a mixture to the teeth of the input pinion gear, the teeth of the ring gear, or the teeth of both the input pinion gear and the ring gear, the mixture consisting essentially of a hypoid gear lubricant and a fluorescing dye; rotating the input pinion gear relative to the housing to thereby drive the ring gear; exposing the portion of the mixture on the teeth of the ring gear to electromagnetic radiation to cause the mixture to fluoresce; and inspecting the fluorescing mixture on the teeth of the ring gear to identify a tooth inspection zone that is indicative of a zone of contact between the teeth of the input pinion gear and the ring gear.

11. The method of claim 10, further comprising determining if the tooth inspection zone is positioned in a desired location.

12. The method of claim 11, further comprising determining if the tooth inspection zone is sized in a desired manner.

13. The method of claim 11, further comprising adjusting a position of the ring gear relative to the input pinion gear if the tooth inspection zone is not positioned in the desired location.

14. The method of claim 10, wherein an amount that is less than or equal to 0.2 ml of the fluorescing dye is contained in 4000 ml of the lubricating oil.

15. The method of claim 10, wherein a sump is employed to hold a lubricant for the input pinion gear and the ring gear during the operation of the assembly and wherein the method further comprises filling the sump with the lubricating oil.

16. The method of claim 15, wherein prior to filling the sump with the lubricating oil, the method further comprises draining the mixture from the assembly.

\* \* \* \* \*